United States Patent [19]

Kleemiss et al.

[11] Patent Number: 5,569,781

[45] Date of Patent: Oct. 29, 1996

[54] PROCESS FOR THE PREPARATION OF 1-AMINOCYCLOPROPANECARBOXYLIC ACID HYDROCHLORIDE

[75] Inventors: Wolfgang Kleemiss, Haltern; Marcel Feld, Köln, both of Germany

[73] Assignee: Huels Aktiengesellschaft, Marl, Germany

[21] Appl. No.: 416,989

[22] Filed: Apr. 5, 1995

[30] Foreign Application Priority Data

Apr. 6, 1994 [DE] Germany .................. 44 11 777.9

[51] Int. Cl.[6] .................................................. C07C 61/04
[52] U.S. Cl. ................................................... 562/506
[58] Field of Search .......................................... 562/506

[56] References Cited

PUBLICATIONS

Chemical Abstracts, vol. 109, No. 15, Oct. 10, 1988, AN–128440e, SU–1313851, May 30, 1987.
Journal of the Chemical Society, Nr. 428, May 1960, pp. 2119–2132, T. A. Conners, et al., "Some Derivatives Of 1–Aminocyclopentanecarboxylic Acid and Related Compounds".

Liu, J. Am. Chem. Soc., vol. 106, pp. 5335–5348 1984.

Pavia, Bull. Soc. Chim., France, pp. 2709–2718 1965.

*Primary Examiner*—Michael L. Shippen
*Attorney, Agent, or Firm*—Oblon, Spivak, McClelland, Maier & Neustadt, P.C.

[57] ABSTRACT

The present invention relates to a novel process for preparing 1-aminocyclopropanecarboxylic acid hydrochloride (ACC·HCl) of the formula

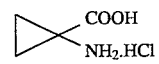

ACC·HCl is prepared from a cyclopropane-1,1-dicarboxylic acid diester via an 1-aminocarbonylcyclopropanecarboxylic acid ester intermediate and an alkali metal salt or alkaline earth metal salt of 1-aminocarbonylcyclopropanecarboxylic acid. The process represents a simplification and gives improved product yields.

8 Claims, No Drawings

PROCESS FOR THE PREPARATION OF 1-AMINOCYCLOPROPANECARBOXYLIC ACID HYDROCHLORIDE

BACKGROUND OF THE INVENTION

1. Field of the Invention

The present invention relates to a novel process for the preparation of 1-aminocyclopropanecarboxylic acid hydrochloride (ACC·HCl)

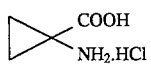

from a cyclopropane-1,1-dicarboxylic acid diester of the formula 1:

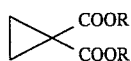

2. Discussion of the Background

The amino acid 1-aminocyclopropanecarboxylic acid (ACC), which can be obtained readily from ACC·HCl by means of an ion exchanger, can be used for a large number of purposes. For example, ACC acts as a plant growth regulator by releasing the plant growth hormone ethylene when catalyzed by an enzyme. Moreover, ACC is employed as a unit in the synthesis of bactericides, fungicides and insecticides. It is therefore desired to find processes which produce ACC in a simple manner, in high yields and in high purity.

Compounds of the formula 1 can be prepared readily from malonic diesters and 1,2-dibromoethane or 1,2-dichloroethane.

SU 1,313,851 describes the synthesis of ACC starting from the diester 1 by the following Scheme I:

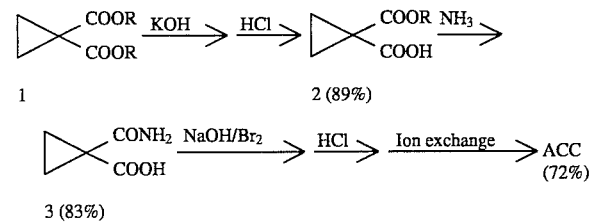

However, the process is very complicated, and the overall yield is low (approximately 50%). In step 1, the starting material is hydrolysed to give the 1,1-cyclopropanecarboxylic acid monoester 2, which is subsequently reacted with ammonia to give the monoamide 3. The sodium salt of ACC is then obtained by means of Hofmann degradation. The amino acid is obtained using ion exchangers.

This process has numerous disadvantages. Firstly, hydrolysis of the diester 1 to give the monoester 2 is very complicated. The diester is stirred with potassium hydroxide at room temperature for 2 days, and the pH is then brought to 1 using concentrated hydrochloric acid. The monoester 2 is then extracted using ethyl acetate. Secondly, the ethyl acetate has to be removed by distillation before the product is reacted with ammonia to give the monoamide 3. In addition, the yields of both reaction steps are only 89% and 83%, respectively. A further disadvantage of the process is the fact that the subsequent Hofmann degradation is carried out batchwise. This operating procedure is not feasible on an industrial scale when batches of a substantial size are used, since the exothermicity of the Hofmann degradation is uncontrollable. In this context, reference is made to DE-A-38 36 917.

A different synthesis, as described by T. A. Connors et al., *J. Chem. Soc.* 2129 (1960), leads to ACC via 4 steps:

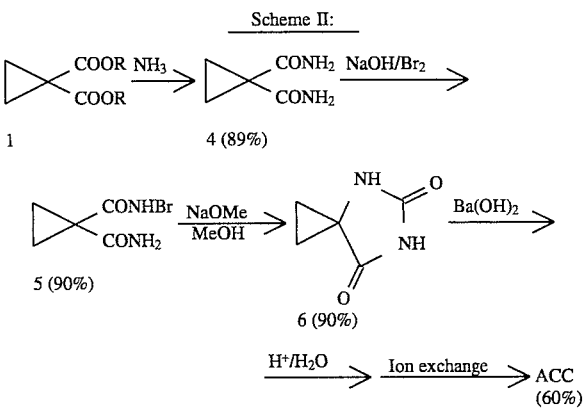

This 4-step synthesis is complicated and involves intermediates which are difficult to manage. The bisamide 4 is sparingly soluble in water, while the bromine-containing product 5 is a highly unstable compound. The overall yield of this synthesis is as little as 35%.

SUMMARY OF THE INVENTION

It is therefore an object of the present invention to find a simple synthesis of ACC·HCl starting from a cyclopropane-1,1-dicarboxylic acid diester, which provides high yields of product and involves few steps.

It is a further object of the present invention to provide a process for producing ACC·HCl in which the intermediates are stable compounds which can be managed easily.

It is a further object of the present invention to carry out a critical step of the synthesis of ACC·HCl (i.e., the Hofmann degradation) in a continuous or semicontinuous manner, to control the exothermicity of the reaction.

These and other objects of the present invention are achieved by producing ACC·HCl from the cyclopropane-1,1-dicarboxylic acid diester of the formula 1 via an 1-aminocarbonylcyclopropanecarboxylic acid ester of the formula 7

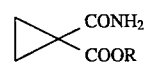

where R is alkyl having 1 to 8 C atoms, and an 1-aminocarbonylcyclopropanecarboxylic acid salt of the formula 8

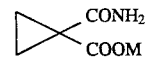

where M is an alkali metal or an alkaline earth metal.

DETAILED DESCRIPTION OF THE PREFERRED EMBODIMENTS

A Hofmann degradation of the salt 8 gives the alkali metal salt or alkaline earth metal salt of ACC, which can be obtained and/or purified via the corresponding hydrochloride and, if desired, converted to the free amino acid, so that the overall reaction sequence may be written as shown in the Scheme III below.

Surprisingly, it has been found that the yield of the first step (the amidation) is >90%, and that hydrolysis to give the salt 8 proceeds virtually quantitatively.

It is a particular advantage of the process that the intermediates 7, 8 and 9 do not have to be isolated, but can in each case be used directly, without work-up, in the step which follows.

Scheme III:

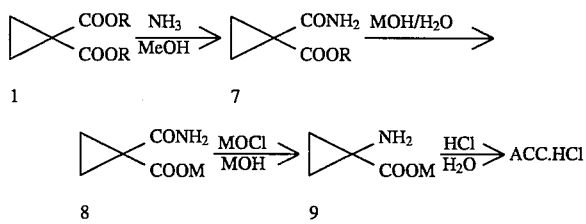

In a first step, the diester 1 is preferably amidated with ammonia in an alcohol to form the monoamidate 7. In a preferred case, the alcohol solvent has 1 to 8 C atoms. In another preferred case, the alcohol has the formula R—OH, corresponding to the alcohol moiety RO— of the diester 1. Examples of suitable alcohol solvents include methanol, ethanol, isopropanol, butanol and hexanol.

In a particular embodiment of the invention, the amidation of the diester 1 is catalyzed by an alkali metal alcoholate or an alkaline earth metal alcoholate. Examples of suitable alkali metal alcoholates include lithium methoxide, lithium ethoxide, lithium propoxide, lithium isopropoxide, lithium n-butoxide, lithium s-butoxide, lithium t-butoxide, sodium methoxide, sodium ethoxide, sodium propoxide, sodium isopropoxide, sodium n-butoxide, sodium s-butoxide, sodium t-butoxide, potassium methoxide, potassium ethoxide, potassium propoxide, potassium isopropoxide, potassium n-butoxide, potassium s-butoxide and potassium t-butoxide. Examples of alkaline earth metal alcoholates include, inter alia, calcium methoxide, calcium ethoxide, calcium propoxide, calcium isopropoxide, calcium n-butoxide, calcium s-butoxide, calcium t-butoxide, barium methoxide, barium ethoxide, barium propoxide, barium isopropoxide, barium n-butoxide, barium s-butoxide and barium t-butoxide.

The monoamidate 7 is obtained in a yield of >95% if a solution of the diester 1 in alcohol is reacted with ammonia at a temperature of from 10° to 120° C. It is interesting to note that the diester 1 can also be amidated successfully without the use of alcoholate as catalyst.

The alcoholic suspension of the monoamidate 7 is subsequently preferably hydrolyzed with about one molar equivalent of an alkali metal hydroxide, more preferably by treating with an aqueous solution of an alkali metal hydroxide. Examples of suitable alkali metal hydroxides include lithium, sodium, potassium, rubidium, cesium and francium hydroxides, preferably sodium and potassium hydroxides. During hydrolyzing, the mixture is heated to a temperature of 10° to 100° C., at least until the solid dissolves. At the same time, the alcohol may be distilled off from the mixture. The yield of the hydrolysis step is virtually quantitative. A homogeneous aqueous solution of the salt 8 is obtained. If a highly-concentrated solution of an alkali metal hydroxide is used, the mixture may be diluted with water after carrying out the hydrolysis so as to obtain a homogeneous solution.

The aqueous solution of the salt 8 is generally employed directly in the Hofmann degradation. It is preferred to react the solution continuously or semicontinuously with a mixture of alkali metal hypochlorite and alkali metal hydroxide solution at 40° to 150° C. under atmospheric pressure or at a pressure up to 5 bar. From 1 to 1.5 molar equivalents of alkali metal hypochlorite and from 1.1 to 4 molar equivalents of alkali metal hydroxide are preferably employed, relative to the salt 8. Suitable alkali metal hydroxides include those mentioned above. Suitable alkali metal hypochlorites include lithium, sodium and potassium hypochlorite.

In the present invention, the alkali metal hypochlorite and alkali metal hydroxide reactants may be added continuously or semicontinuously to the reaction mixture at pre-specified rates, such as from 0.01 molar equivalents of alkali metal hypochlorite and 0.011 molar equivalents of alkali metal hydroxide per hour to 6 molar equivalents of alkali metal hypochlorite and 16 molar equivalents of alkali hydroxide per hour. The rates of addition of the alkali metal hypochlorite and alkali metal hydroxide reactants may be independent of each other. In this embodiment, the reaction temperature may be monitored so as not to exceed a temperature at which the reaction components are known to decompose. It is preferred not to allow the Hofmann degradation to exceed a temperature of 150° C. A semicontinuous reaction may be conducted by adding successive portions of the alkali metal hypochlorite/alkali metal hydroxide solution(s) (for example, of from 1% to 50% by volume of the total solution(s) employed) over the course of the reaction, such that the reaction temperature does not exceed the decomposition temperature of any of the components (i.e., the reactants or the product of the formula 9) until the entire quantity of hypochlorite/hydroxide solution has been added.

The pH of the alkali product of the Hofmann degradation can be adjusted to 1 to 2 by adding a hydrochloric acid solution, preferably an aqueous hydrochloric acid solution having an HCl concentration of from 5% to 37% by weight. The reaction mixture can subsequently be evaporated and the ACC·HCl dissolved out of the residue using a $C_1$–$C_6$ alkanol, preferably ethanol, so as to remove it from the sodium chloride in this manner. The alcoholic ACC·HCl solution is then re-evaporated. Any remaining impurities can be removed by washing, for example using hot acetone. This gives ACC·HCl from the diester 1 in a yield of approximately 80%. From the ACC·HCl, the free amino acid ACC can be obtained by conventional methods (for example, by contacting a solution of ACC·HCl with an ion exchanger).

When carrying out the present process in practice, the diester 1 is amidated to give the monoamidate 7, preferably with ammonia at a temperature of from 0° to 100° C., more preferably at 20° to 60° C., under an $NH_3$ pressure of from 1 to 5 bar, more preferably at 1 bar, in an alcoholic solution. The solvent used may be a $C_1$–$C_8$ alkanol, preferably an alcohol of the formula R—OH corresponding to the alcohol moiety of the diester 1.

The amidation step can be accelerated by using 1 to 40 mol % of at least one alkali metal alcoholate as catalyst. It is also possible to use one or more alkaline earth metal alcoholates, such as, for example, a magnesium alcoholate, as a catalyst. In general, the alcohol of the alcoholate has 1 to 8 C atoms, and alcoholates of lower alcohols ($C_1$–$C_4$ alkanols) are preferably used.

In the present process, the monoamide 7 is furthermore preferably hydrolysed to give the salt 8 using a 1 to 40% aqueous solution of an alkali metal hydroxide at a temperature of preferably from 25° to 50° C., without hydrolysing the amide function in the process. In a preferred embodiment, a dilute sodium hydroxide solution may be added directly to the suspension of the monoamide 7 in alcohol, and the alcohol may subsequently be distilled off from the mixture. This gives an aqueous solution of the salt 8.

It is an advantage of the present process that the Hofmann degradation of the salt 8 can be carried out continuously. The aqueous solution of the salt 8 is combined with a mixture of (i) a 5 to 14% by weight alkali metal hypochlorite solution and (ii) 1.1 to 4 (preferably from 1.5 to 3) molar equivalents of an alkali metal hydroxide, preferably in a 10 to 50% by weight solution, at a temperature of from 10° to 60° C., and subsequently brought to a temperature preferably of from 60° to 100° C. (for example, in a continuous reaction using a reaction tube).

The pH of the alkaline reaction product of the Hofmann degradation can be brought to a value of from 1 to 2 using hydrochloric acid. A mixture (if appropriate, an aqueous mixture) of the amino acid hydrochloride and the alkali metal chloride is obtained by evaporating the solvent (if appropriate, the water) from the mixture.

Extraction with a $C_1$–$C_6$ alkanol gives a solution of ACC·HCl in alcohol, and this solution may be reconcentrated prior to any subsequent steps. Any remaining impurities can be removed from the product by washing, for example, with acetone. ACC·HCl is obtained in a yield of >75% in most cases, at a purity of >99%.

Other features of the present invention will become apparent in the course of the following descriptions of exemplary embodiments which are given for illustration of the invention, and are not intended to be limiting thereof. Thus, the present invention will be better understood as exemplified by the following examples, which are not intended to limit the invention in any manner.

EXAMPLES

Example (1): Preparation of Methyl 1-aminocarbonylcyclopropanecarboxylate

Ammonia (20 l/h) is passed at 20° C. into a solution of 1,106 g (7 mol) of dimethyl cyclopropanedicarboxylate in 700 ml of methanol, with stirring. After approximately 10 hours, addition of $NH_3$ is stopped, and the reaction mixture is cooled to 8° C. The solid formed is filtered off with suction, then washed using 200 g of cold methanol. After drying the product, 926.2 g (92.5%) of methyl 1-aminocarbonylcyclopropanecarboxylate are obtained (m.p.: 157° C.).

Example (2): Preparation of 1-aminocarbonylcyclopropanecarboxylic Acid

Ammonia (20 l/h) is passed at 20° C. into a solution of 1,106 g (7 mol) of dimethyl cyclopropane-1,1-dicarboxylate in 700 ml of methanol, with stirring. After approximately 10 hours, addition of $NH_3$ is stopped.

1.4 l of 20% sodium hydroxide solution are added to the suspension, and the mixture is heated to 40° C. The methanol is distilled off in vacuo. When the mixture is cold, 680 g of concentrated hydrochloric acid are added, whereupon the product precipitates. It is filtered off with suction, washed with cold water and dried (m.p.: 182° C.). Yield: 813 g, 90%.

If it is intended to degrade the 1-aminocarbonylcyclopropanecarboxylic acid to give ACC, then neutralizing with hydrochloric acid is not necessary. In this case, the aqueous solution of sodium 1-aminocarbonylcyclopropanecarboxylate is reacted directly with a mixed sodium hypochlorite and sodium hydroxide solution (see: Example (4), part (c) below).

Example (3): Preparation of 1-aminocyclopropanecarboxylic Acid Hydrochloride (ACC·HCl) Via the Alkali Metal Salt of 1-aminocarbonylcyclopropanecarboxylic Acid 143 g (1 mol) of methyl 1-aminocarbonylcyclopropanecarboxylate (e.g., as prepared in Example (1)) is introduced into 540 g of 7.4% sodium hydroxide solution, and the suspension is slowly heated to 40° C., with stirring. After 20 minutes, the reaction mixture is homogeneous and is allowed to cool to room temperature. This solution (Solution A) is retained for the next step. The methanol liberated during the reaction can also be distilled off before the solution is employed in the next step.

The other solution required for the next step is prepared from 756.6 g (1.25 mol) of 12.3% sodium hypochlorite solution and 267 g (2 mol) of 30% sodium hydroxide solution (Solution B).

Solution A and Solution B, in each case at room temperature, are pumped into a mixing vessel over the course of 1 hour. The reaction mixture is subsequently passed through a tubular reactor whose temperature is kept at 80° C. (residence time: 3.5 minutes). The homogeneous reaction product has a pH of 11. The pH of the mixture is brought to 1 by adding 400 ml (4 mol) of concentrated hydrochloric acid. The acidic solution is subsequently evaporated to dryness, during which the mixture temperature must not exceed 60° C. ACC·HCl is now dissolved out of the residue using 4,800 ml of ethanol, and the ethanol solution is separated off from the sodium chloride by filtration. The ethanol extract is then evaporated to dryness, the residue is stirred into 200 g of hot acetone, and the mixture is subsequently filtered. After drying of the filter residue, 110 g (80%) of ACC·HCl are obtained (purity: 98%).

Example (4)

(a) Ammonia (20 l/h) is passed at room temperature into a solution of 1,106 g (7 mol) of dimethyl cyclopropane-1,1-dicarboxylate in 700 ml of methanol, with stirring. After approximately 10 hours, addition of $NH_3$ is stopped.

(b) 1.4 l of 20% sodium hydroxide solution are added to the suspension, and the mixture is heated to 40° C. The methanol is distilled off in vacuo. This gives Solution A.

The other solution required for the next step is prepared by mixing 756.6 g (1.25 mol) of 12.3% sodium hypochlorite solution and 267 g (2 mol) of 30% sodium hydroxide solution (Solution B).

(c) Solution A and Solution B, in each case at 20° C., are pumped into a mixing vessel over the course of 1 hour and subsequently passed through a tubular reactor whose temperature is kept at 80° C. (residence time: approx. 3.5 minutes). The homogeneous reaction product has a pH of 11. The pH of the mixture is brought to 1 by adding 400 ml (4 mol) of concentrated hydrochloric acid. The acidic solution is subsequently evaporated to dryness, during which process the mixture temperature must not exceed 60° C. ACC·HCl is now dissolved out of the residue using 4,800 ml of ethanol, and separated off from the sodium chloride by filtration. The ethanol extract is also evaporated to dryness, the residue is stirred into 200 g of hot acetone, and the mixture is subsequently filtered. After drying of the filter residue, 725 g (76%) of ACC·HCl are obtained (purity: 98%).

Obviously, numerous modifications and variations of the present invention are possible in light of the above teachings. It is therefore to be understood that within the scope of the appended claims, the invention may be practiced otherwise than as specifically described herein.

What is claimed and desired to be secured by Letters Patent of the United States is:

1. A process for the preparation of 1-aminocyclopropanecarboxylic acid hydrochloride, comprising reacting a cyclopropane-1,1-dicarboxylic acid diester of the formula

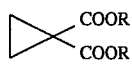

with ammonia to form a 1-aminocarbonylcyclopropanecarboxylic acid ester of the formula 7

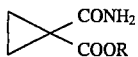 7 wherein R is a $C_1$–$C_8$ alkyl group, hydrolyzing said 1-aminocarbonylcyclopropanecarboxylic acid ester of the formula 7 to form an 1-aminocarbonylcyclopropanecarboxylic acid salt of the formula 8

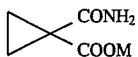 8 wherein M is an alkali metal or alkaline earth metal, reacting said 1-aminocarbonylcyclopropanecarboxylic acid salt of the formula 8 with a mixture of an alkali metal hypochlorite and an alkali metal hydroxide to form an 1-cyclopropanecarboxylic acid salt of the formula 9

 9 and adding a sufficient amount of hydrochloric acid to said 1-aminocyclopropanecarboxylic acid salt to form said 1-aminocyclopropanecarboxylic acid hydrochloride.

2. The process of claim 1, wherein said cyclopropane-1,1-dicarboxylic acid diester of the formula 1 is reacted with ammonia in an alcohol to give the 1-aminocarbonylcyclopropanecarboxylic acid ester of the formula 7.

3. The process of claim 2, wherein said alcohol has 1 to 8 C atoms.

4. The process of claim 2, wherein said the reaction of said cyclopropane-1,1-dicarboxylic acid diester of the formula 1 to give the 1-aminocarbonylcyclopropanecarboxylic acid ester of the formula 7 further comprises catalyzing said reaction with an alkaline earth metal alcoholate or alkaline earth metal alcoholate.

5. The process of claim 2, wherein said 1-aminocarbonylcyclopropanecarboxylic acid ester of the formula 7 is hydrolysed with an equivalent of an aqueous alkali metal hydroxide solution to give the alkali metal salt of 1-aminocarbonylcyclopropanecarboxylic acid of the formula 8.

6. The process of claim 5, wherein the subsequent reaction of the alkali metal salt of the 1-aminocarbonylcyclopropanecarboxylic acid of the formula 8 proceeds continuously or semicontinuously with a mixture of alkali metal hypochlorite and an alkali metal hydroxide solution at 40° to 150° C.

7. The process of claim 6, wherein the pH of the reaction product is adjusted to a value of from 1 to 2 using hydrochloric acid and 1-aminocyclopropanecarboxylic acid hydrochloride is isolated in solid form from the resulting aqueous solution.

8. The process of claim 1, wherein said intermediates 7, 8 and 9 are not isolated but introduced in each case directly into the next step.

* * * * *